(12) United States Patent
Hamaguchi et al.

(10) Patent No.: US 8,355,778 B2
(45) Date of Patent: Jan. 15, 2013

(54) TRUNK WIDTH MEASURING UNIT AND VISCERAL FAT MEASURING DEVICE

(75) Inventors: Takehiro Hamaguchi, Kyoto (JP); Hiromichi Karo, Kyoto (JP); Yasuaki Murakawa, Kyoto (JP); Tomoya Ijiri, Kameoka (JP); Shojiro Oku, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/023,104

(22) Filed: Feb. 8, 2011

(65) Prior Publication Data

US 2011/0137198 A1 Jun. 9, 2011

Related U.S. Application Data

(63) Continuation of application No. PCT/JP2009/066409, filed on Sep. 18, 2009.

(30) Foreign Application Priority Data

Sep. 22, 2008 (JP) ................................ 2008-243167

(51) Int. Cl.
*A61B 5/00* (2006.01)
(52) U.S. Cl. ........................ 600/547; 600/587
(58) Field of Classification Search .................. 600/547, 600/587
See application file for complete search history.

(56) References Cited

U.S. PATENT DOCUMENTS

| 2004/0077969 | A1 | 4/2004 | Onda et al. |
| 2005/0107717 | A1 | 5/2005 | Yamamoto et al. |
| 2005/0222516 | A1 | 10/2005 | Kasahara et al. |
| 2008/0021349 | A1 | 1/2008 | Sakai et al. |

FOREIGN PATENT DOCUMENTS

| JP | A-2001-212111 | 8/2001 |
| JP | A-2002-238871 | 8/2002 |
| JP | A-2005-103198 | 4/2005 |
| JP | A-2005-288023 | 10/2005 |
| JP | A-2006-34598 | 2/2006 |
| JP | A-2007-130072 | 5/2007 |
| JP | A-2007-175142 | 7/2007 |
| JP | A-2008-23232 | 2/2008 |
| JP | A-2008-49114 | 3/2008 |

OTHER PUBLICATIONS

International Search Report dated Oct. 27, 2009 in International Patent Application No. PCT/JP2009/066409.

*Primary Examiner* — Max Hindenburg
(74) *Attorney, Agent, or Firm* — Oliff & Berridge, PLC

(57) ABSTRACT

To provide a trunk width measuring unit capable of improving reliability of measurement precision, and a visceral fat measuring device. The trunk width measuring unit is provided with a first contact portion to be brought into contact with an upper surface of a trunk of a user in a supine position, a second contact portion to be brought into contact with one of side surfaces of the trunk, a third contact portion to be brought into contact with the other side surface of the trunk, and a trunk width calculating unit for calculating vertical width and horizontal width of the trunk from height from an upper surface of a bed to a contact position of the first contact portion and a distance between the second contact portion and the third contact portion.

9 Claims, 8 Drawing Sheets

TRUNK WIDTH MEASURING UNIT AND VISCERAL FAT MEASURING DEVICE

TECHNICAL FIELD

The present invention relates to a trunk width measuring unit and a visceral fat measuring device provided with this.

BACKGROUND ART

In recent years, as a method of measuring an abdominal fat such as a visceral fat and a subcutaneous fat, a method of using bioelectrical impedance information and physical information of a user is examined. With this method, the bioelectrical impedance is measured with using electrodes in contact with a trunk or the like of the user, and a circumferential length, vertical width, horizontal width, and the like of the trunk are measured as the physical information.

For example, patent document 1 proposes a visceral fat measuring device in which a plurality of electrodes for measuring the bioelectrical impedance is arranged, an electrode support portion capable of being deflected along a shape of the trunk and pressed onto a front surface of an abdominal part of the trunk so as to closely attach the electrodes onto a surface of the trunk, and a pair of arm portions to be brought into contact with both sides of the abdominal part so as to measure the horizontal width of the trunk are provided, and indicators relating to a body fat are calculated from the bioelectrical impedance and the horizontal width of the trunk. Patent document 2 proposes a trunk impedance type body composition monitor for estimating the indicators relating to the body fat from the bioelectrical impedance of the trunk detected by nipping the trunk from the front and back sides by a support portion including a support surface in which a plurality of electrodes is arranged and a pressed portion including a pressed surface facing the support surface, and the vertical width of the trunk measured based on a stop position of the pressed surface.

However, with these technologies, since the pressed portion for closely attaching the electrodes also serves as a measuring unit of the physical information, and the information measured as the physical information of the user is only the horizontal width or the vertical width of the trunk, there is a problem that reliability is insufficient for precision of the information. That is, the trunk of a human being is a part where a shape is easily changed by a breathing action. A section of the abdominal part is changed so that at the time of inhalation, the vertical width is extended and the horizontal width is contracted, and at the time of exhalation, the vertical width is contracted and the horizontal width is extended. Therefore, measurement values are differentiated between a case where the horizontal width or the vertical width of the trunk is measured upon the inhalation and a case where the horizontal width or the vertical width is measured upon the exhalation, so that calculation of the indicators relating to the body fat is varied.

Therefore, in a case where size of the trunk is used as the physical information, it can be said that a breathing state is desirably reflected to size information of the trunk, that is, the breathing state is desirably reflected so as to acquire the size information of the trunk.

RELATED ART DOCUMENT

Patent Document

[Patent Document 1]: Japanese Unexamined Patent Publication No. 2005-288023

[Patent Document 2]: Japanese Unexamined Patent Publication No. 2008-23232

DISCLOSURE OF THE INVENTION

Problems to be Solved by the Invention

An object of the present invention is to provide a trunk width measuring unit capable of improving reliability of measurement precision, and a visceral fat measuring device.

Means for Solving the Problem

In the present invention, the following means are adopted in order to solve the above problem.

That is, a trunk width measuring unit of the present invention includes a first contact portion to be brought into contact with an upper surface of a trunk of a user in a supine position, a second contact portion to be brought into contact with one of side surfaces of the trunk, a third contact portion to be brought into contact with the other side surface of the trunk, and a trunk width calculating unit for calculating vertical width and horizontal width of the trunk from height from a plane on which the user lies to a contact position of the first contact portion and a distance between the second contact portion and the third contact portion.

According to the present invention, since the vertical width and the horizontal width of the trunk can be measured at the same breathing timing, a breathing state (at the time of inhalation or exhalation) can be reflected in measurement of the vertical width and the horizontal width of the trunk.

The trunk width measuring unit may have a unit main body in which the first contact portion is attached movably in the vertical direction, the second contact portion and the third contact portion are attached movably in the horizontal direction, and the second contact portion or the third contact portion is placed at a position where the contact portion is brought into contact with the side surface of the trunk of the user.

According to this configuration, by changing positions of the contact portions relative to the unit main body in accordance with size of the horizontal width of the trunk of the user, the vertical width and the horizontal width of the trunk can be measured.

The trunk width measuring unit may further have a first detector for detecting a lowering distance of the first contact portion from an original position on the upper side of the trunk of the user to a contact point with the upper surface of the trunk, a second detector for detecting a moving distance of the second contact portion from an original position in the horizontal direction, and a third detector for detecting a moving distance of the third contact portion from an original position in the horizontal direction, wherein the trunk width calculating unit may calculate the height from the plane on which the user lies to the contact position of the first contact portion based on the moving distance of the first contact portion detected by the first detector, and calculate the distance between the second contact portion and the third contact portion based on the moving distance of the second contact portion detected by the second detector and the moving distance of the third contact portion detected by the third detector.

According to this configuration, by detecting displacement distances of the contact portions from the original positions to contact points with the surface of the trunk, the vertical width and the horizontal width of the trunk can be easily measured.

The first contact portion, the second contact portion and the third contact portion may be movable so as to follow a change in a shape of the trunk in time of breathing of the user.

Thereby, the breathing state can be more precisely reflected in the measurement of the vertical width and the horizontal width of the trunk, so that measurement precision can be improved.

The trunk width measuring unit may have an original position sensor for detecting whether or not the first contact portion, the second contact portion and/or the third contact portion is placed at the original position.

Thereby, whether or not the contact portion is placed at the original position can be a factor of determining whether or not the contact portion is in contact with the trunk.

The trunk width measuring unit may have an excessive press sensor for detecting whether or not the second contact portion or the third contact portion is placed at a movable limit position.

Thereby, deformation of the trunk due to pressing of the trunk exceeding the movable limit position of the second contact portion or the third contact portion can be prevented.

The trunk width measuring unit may have a pressure sensor for detecting reactive force that the second contact portion and/or the third contact portion receives from the trunk of the user.

Thereby, a contact state between the trunk and the second contact portion or the third contact portion and the breathing state of the user can be determined based on a magnitude of the reactive force.

Part or all of the first contact portion, the second contact portion and/or the third contact portion may be formed by a transparent or semi-transparent member.

Thereby, a contact state between the contact portion and the surface of the trunk can be easily visually recognized. Therefore, whether or not the contact position of the contact portion is correct, whether or not the contact portion is excessively pressed onto the trunk, or the like can be easily confirmed, so that the vertical width and the horizontal width of the trunk can be accurately measured.

The trunk width calculating unit may calculate maximum values, minimum values, and average values of the vertical width and the horizontal width of the trunk in time of breathing from the moving distances of the first contact portion, the second contact portion and the third contact portion, and any of the values may be measurement values of the vertical width and the horizontal width of the trunk.

Thereby, the breathing state can be more precisely reflected in the measurement of the vertical width and the horizontal width of the trunk, so that the measurement precision can be improved.

In order to achieve the above object, a visceral fat measuring device of the present invention includes the above trunk width measuring unit, and in the visceral fat measuring device, a visceral fat amount is calculated based on a trunk sectional area in a section on an abdominal part of the trunk vertical to a body axis of the trunk, the trunk sectional area being calculated from the vertical width and the horizontal width of the trunk obtained with using the trunk width measuring unit, impedance information of the entire trunk obtained by applying an electric current from hands and legs to the trunk and measuring a potential difference in part of a surface of the trunk, and impedance information of a surface layer of the trunk obtained by applying the electric current through the vicinity of the surface layer of the trunk and measuring a potential difference in part of the surface of the trunk.

According to the present invention, the visceral fat amount can be measured from the trunk sectional area, the impedance information of the entire trunk, and the impedance information of the surface layer of the trunk. The trunk sectional area can be calculated based on the vertical width and the horizontal width of the trunk. Since the impedance information can be obtained by measuring the potential difference in a state that the electric current is applied to a human body (a living body), the impedance information can be also easily obtained. Therefore, the visceral fat amount can be relatively easily and noninvasively measured. It should be noted that the "visceral fat amount" in the present invention includes indicators showing the visceral fat amount such as a visceral fat sectional area, a visceral fat volume, and a ratio of the visceral fat sectional area relative to an abdominal sectional area.

According to the present invention, the trunk width measuring unit for measuring the vertical width and the horizontal width of the trunk of the user is provided. Therefore, since the visceral fat amount is calculated with using two measurement values including the vertical width and the horizontal width of the trunk of the user as physical information of the user, an influence of the change in the shape of the trunk due to breathing is reduced, so that the measurement precision can be improved.

In the device described in the above patent document 2, since the pressed portion for closely attaching the electrodes also serves as the measuring unit of the physical information, and the trunk is sometimes deformed due to pressing force and weight of the pressed portion, there is a problem that reliability is insufficient for the precision of the information. That is, when pressing strength of the electrodes is varied, the varied strength emerges as varied contact resistance between the electrodes and the surface of the body, and the measurement precision is sometimes lowered. Therefore, there is a need for stably pressing the electrodes onto the trunk at a fixed load. However, due to a magnitude of the force of pressing the pressed portion, or due to a magnitude of the weight of the pressed portion in which a plurality of parts such as the electrodes is integrated, the trunk is deformed due to the pressing of the pressed portion. In this case, the measurement values of the shape of the trunk are also varied.

However, according to the present invention, the electrodes for measuring the impedance information are separated from the trunk width measuring unit for measuring the vertical width and the horizontal width of the trunk. Thus, unlike the conventional technology, there is no need for pressing the contact portions to be brought into contact with the trunk onto the surface of the trunk so that the electrodes are closely attached to the surface of the trunk but the contact portions are only required to be in contact with the surface of the trunk. Therefore, the deformation of the trunk due to contact of the contact portions for the measuring the vertical width and the horizontal width of the trunk can be suppressed, so that generation of varied calculated values of the shape of the trunk can be suppressed.

It should be noted that the above configurations can be combined and adopted as far as possible.

Effect of the Invention

As described above, according to the present invention, the reliability of the measurement precision can be improved.

BEST MODE FOR CARRYING OUT THE INVENTION

Modes for carrying out this invention will be described in detail as examples with reference to the drawings based on an embodiment. However, the scope of this invention is not limited to size, materials, shapes, relative arrangement, and the like of constituent elements described in the embodiment unless specifically described.

(Embodiment)

With reference to FIGS. 1 to 8, a visceral fat measuring device according to the embodiment of the present invention will be described.

(Measurement Principle of Visceral Fat)

Figure 1:
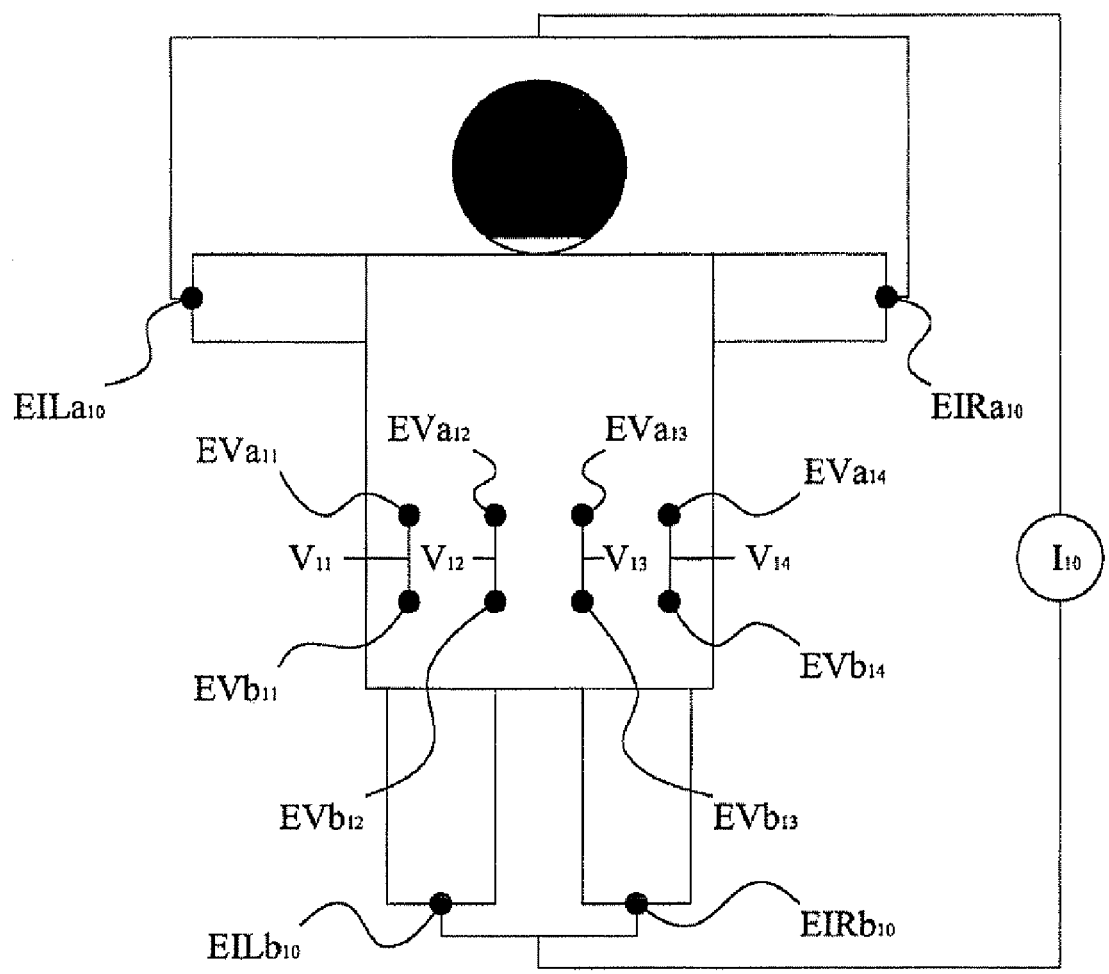
FIG. 1 is a schematic view showing a state when impedance is measured.
Figure 2:
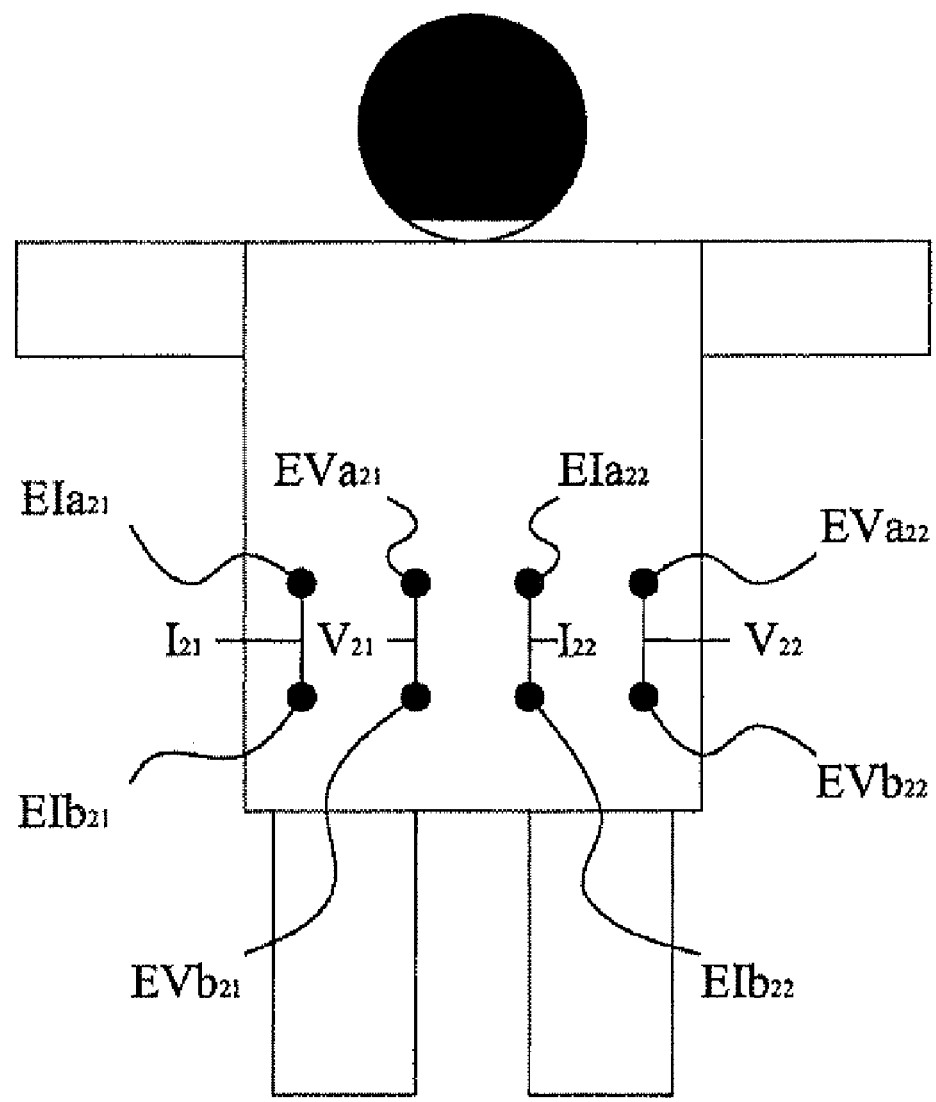
FIG. 2 is a schematic view showing a state when impedance is measured.

With reference to FIGS. 1 and 2, a measurement principle of a visceral fat in the visceral fat measuring device according to the embodiment of the present invention will be described. FIGS. 1 and 2 are schematic views showing states when impedance is measured. It should be noted that FIGS. 1 and 2 show states seen from the dorsal side of a user subjected to measurement of the visceral fat.

FIG. 1 shows the state in a case where impedance information of the entire trunk is obtained. As shown in the figure, electrodes EILa10, EIRa10 are respectively attached to both hands of the user subjected to the measurement of the visceral fat. Electrodes EILb10, EIRb10 are also respectively attached to both legs of the user. Pairs of electrodes provided side by side in the body axis direction of the trunk are attached at four points in the horizontal width direction of the trunk on the dorsal side of the trunk of the user. That is, the total of eight electrodes EVa11, EVb11, EVa12, EVb12, EVa13, EVb13, EVa14, EVb14 are attached.

In this state, an electric current I10 passing through the trunk is applied with using the electrodes EILa10, EIRa10, EILb10, EIRb10 respectively attached to the both hands and the both legs. A potential difference V11 is measured with using a pair of the electrodes EVa11, EVb11, a potential difference V12 is measured with using a pair of the electrodes EVa12, EVb12, a potential difference V13 is measured with using a pair of the electrodes EVa13, EVb13, and a potential difference V14 is measured with using a pair of the electrodes EVa14, EVb14. That is, the potential differences in part of a surface of the trunk are measured at the four points on the dorsal side.

Impedance Zt of the entire trunk is calculated from the potential differences measured in such a way. It should be noted that by measuring the potential differences V11, V12, V13, V14 at the four points and calculating the impedance of the entire trunk with using an average value thereof, an influence of varied fat distribution in the trunk, and the like can be reduced.

In a case where the electric current I10 is applied from the both hands and the both legs which are distant from the trunk, almost all the electric current I10 passes through a part where electric resistance is low, that is, a part other than a fat. Therefore, the impedance Zt of the entire trunk calculated from the potential differences V11, V12, V13, V14 measured with using such an electric current I10 is largely influenced by an amount of lean body (viscera, muscles, and skeletons) excluding the fat. Therefore, a lean body sectional area Sa (estimated value) can be calculated from this impedance Zt.

FIG. 2 shows the state in a case where impedance information of a surface layer of the trunk on the dorsal side of the trunk is obtained. As shown in the figure, pairs of electrodes provided side by side in the body axis direction of the trunk are attached at four points in the horizontal width direction of the trunk on the dorsal side of the trunk of the user. That is, the total of eight electrodes EIa21, EIb21, EVa21, EVb21, EIa22, EIb22, EVa22, EVb22 are attached.

In this state, an electric current I21 is applied with using a pair of the electrodes EIa21, EIb21, and an electric current I22 is applied with using a pair of the electrodes EIa22, EIb22. It should be noted that a current value of the electric current I21 and a current value of the electric current I22 are the same. A potential difference V21 is measured with using a pair of the electrodes EVa21, EVb21, and a potential difference V22 is measured with using a pair of the electrodes EVa22, Evb22. That is, the potential differences in part of the surface of the trunk are measured at the two points on the dorsal side.

Impedance Zs of the surface layer on the dorsal side of the trunk is calculated from the potential differences measured in such a way. It should be noted that by measuring the potential differences V21, V22 at the two points and calculating the impedance Zs of the surface layer of the trunk with using an average value thereof, an influence of varied subcutaneous fat and the like can be reduced. It should be noted that by switching a circuit so that the electrodes for applying the electric current serve as electrodes for measuring the potential differences, and the electrodes for measuring the potential differences serve as electrodes for applying the electric currents, the potential differences can be measured at the four points. In such a way, the influence of the varied subcutaneous fat and the like can be furthermore reduced.

In a case where the electric currents I21, I22 are applied by a pair of the electrodes attached at the positions on the back side of an abdominal part on the dorsal, almost all the electric currents I21, I22 pass through the surface layer of the trunk. Therefore, the impedance Zs of the surface layer of the trunk calculated from the potential differences V21, V22 measured with using such electric currents I21, I22 is largely influenced by an amount of a subcutaneous fat amount. Therefore, a subcutaneous fat sectional area Sb (estimated value) can be calculated from this impedance Zs.

Therefore, when a trunk sectional area (an area of a section on the abdominal part of the trunk vertical to a body axis of the trunk) is St, a visceral fat sectional area Sx is Sx=St−Sa−Sb. Thus, the visceral fat sectional area Sx can be calculated.

The trunk sectional area St can be calculated from a circumferential length of a waist part (waist length) or vertical width and horizontal width of the trunk (in the vicinity of the abdominal part). For example, in a case of calculating from the vertical width and the horizontal width of the trunk, when the horizontal width of the trunk is 2a, and the vertical width is 2b, the section of the trunk is substantially oval. Thus, the trunk sectional area is substantially π×a×b. However, this value is highly susceptible to an error. Thus, by multiplying a coefficient for correcting the error, a more precise trunk sectional area St can be obtained. With regard to this coefficient, for example based on a large number of X ray CT image samples, an optical value of α can be determined from a relationship between a trunk sectional area St' obtained from the X ray CT images, and a value a, and a value b so as to satisfy St'=α×π×a×b.

Thereby, based on the horizontal width 2a and the vertical width 2b of the trunk, the trunk sectional area St (=α×π×a×b) with less error can be calculated. It should be noted that since the value α multiplied for correction may have an optimal value appropriately differentiated in accordance with gender, age, body height, weight, and the like (hereinafter, these are called as user information), by changing the value a in accordance with the user subjected to the measurement, the more precise trunk sectional area St can be calculated.

As described above, the lean body sectional area Sa can be calculated from the impedance Zt of the entire trunk. However, the lean body sectional area Sa cannot be calculated only with the impedance Zt of the entire trunk. That is, there is a need for converting a value proportional to size of the trunk obtained from the impedance Zt into the lean body sectional area Sa. More specifically, for example, the lean body sectional area Sa can be expressed as Sa=β×a×(1/Zt).

The value a is a half of the horizontal width of the trunk as described above, which is a value relating to the size of the trunk. This value is not limited to this. For example, (a×b) may be used so that values of the vertical width and the horizontal width of the trunk are reflected, the trunk sectional area St may be used, or the circumferential length of the waist part (the waist length) may be used.

The value β is a coefficient for converting into the lean body sectional area Sa, and an optimal value thereof can be determined from a large number of the X ray CT image samples as well as a case where the value α is determined. That is, based on a large number of the X ray CT image samples, the optimal value of β can be determined from a relationship between a lean body sectional area Sa' obtained from the X ray CT images, and the value a, and the impedance Zt of the entire trunk of a person subjected to the X ray CT images so as to satisfy Sa'=β×a(1/Zt).

Further, as described above, the subcutaneous fat sectional area Sb can be calculated from the impedance Zs of the surface layer of the trunk on the back side of the abdominal part on the dorsal. However, the subcutaneous fat sectional area Sb cannot be calculated only with the impedance Zs of the surface layer. That is, there is a need for converting a value proportional to the size of the trunk obtained from the impedance Zs into the subcutaneous fat sectional area Sb. More specifically, the subcutaneous fat sectional area Sb can be expressed as Sb=γ×a×Zs.

The value a is the half of the horizontal width of the trunk as described above, which is the value relating to the size of the trunk. This value is not limited to this. For example, (a×b) may be used so that values of the vertical width and the horizontal width of the trunk are reflected, the trunk sectional area St may be used, or the circumferential length of the waist part (the waist length) may be used.

The value γ is a coefficient for converting into the subcutaneous fat sectional area Sb, and an optimal value thereof can be determined from a large number of the X ray CT image samples as well as a case where the value α is determined. That is, based on a large number of the X ray CT image samples, the optimal value of γ can be determined from a relationship between a subcutaneous fat sectional area Sb' obtained from the X ray CT images, and the value a, and the impedance Zs of the surface layer of the trunk of the person subjected to the X ray CT images so as to satisfy Sb'=γ×a×Zs.

It should be noted that the above values β and γ may have optical values appropriately differentiated in accordance with the user information as well as the value α used in a case where the sectional area of the abdominal part is determined. Therefore, by changing the values β and γ in accordance with the user subjected to the measurement, more precise lean body sectional area Sa and subcutaneous fat sectional area Sb can be calculated.

As described above, in the visceral fat measuring device according to the present embodiment, the visceral fat sectional area Sx is calculated from the trunk sectional area St, the lean body sectional area Sa calculated based on the impedance Zt of the entire trunk, and the subcutaneous fat sectional area Sb calculated based on the impedance Zs of the surface layer of the trunk.

That is, the visceral fat sectional area is expressed as Sx=St−Sa−Sb.

In this case, St=α×π×a×b, Sa=β×a×(1/Zt), and Sb=γ×a×Zs are established. Then, the value a is the half of the horizontal width of the trunk, and the value b is a half of the vertical width of the trunk. The values α, β, γ are the coefficients obtained based on a large number of the X ray CT image samples for determining the optimal values of St, Sa, Sb. It should be noted that these coefficients can be changed in accordance with the user information as described above.

As clear from the above expression, the measured (calculated) visceral fat amount is the visceral fat sectional area. However, the visceral fat amount as a measurement result is not limited to the visceral fat sectional area but may be a ratio of the visceral fat sectional area relative to the trunk sectional area, or a visceral fat volume converted from the visceral fat sectional area.

It should be noted that as clear from the above expression, the measurement principle of the visceral fat in the visceral fat measuring device according to the embodiment of the present invention is based on a thought that the visceral fat sectional area Sx can be obtained by subtracting the lean body sectional area Sa and the subcutaneous fat sectional area Sb from the trunk sectional area St.

However, the visceral fat measuring device according to the present invention is not always limited to simple adoption of the above expression Sx=St−Sa−Sb, but also includes application of such a principle.

For example, the visceral fat sectional area Sx can be determined from Sx=St−Sa−Sb+δ (δ is a correction amount). That is, with similar methods to a case where the above values α, β, γ are determined, the correction amount δ can be added based on a large number of the X ray CT image samples.

The visceral fat sectional area Sx can be determined from Sx=St−F (Zt, Zs, a, b). It should be noted that F (Zt, Zs, a, b) is a function having Zt, Zs, a, b as parameters.

That is, a total value of the lean body sectional area Sa and the subcutaneous fat sectional area Sb has a correlation with the impedance Zt of the entire trunk, the impedance Zs of the surface layer of the trunk, and the size of the trunk (the vertical width and the horizontal width of the trunk in the present embodiment). Therefore, the total value of the lean body sectional area Sa and the subcutaneous fat sectional area Sb can be determined from the function F (Zt, Zs, a, b) having the values t, Zs, a, b as the parameters. It should be noted that this function F (Zt, Zs, a, b) can also be derived from a large number of the X ray CT image samples.

(Entire Configuration of Visceral Fat Measuring Device)

Figure 3:
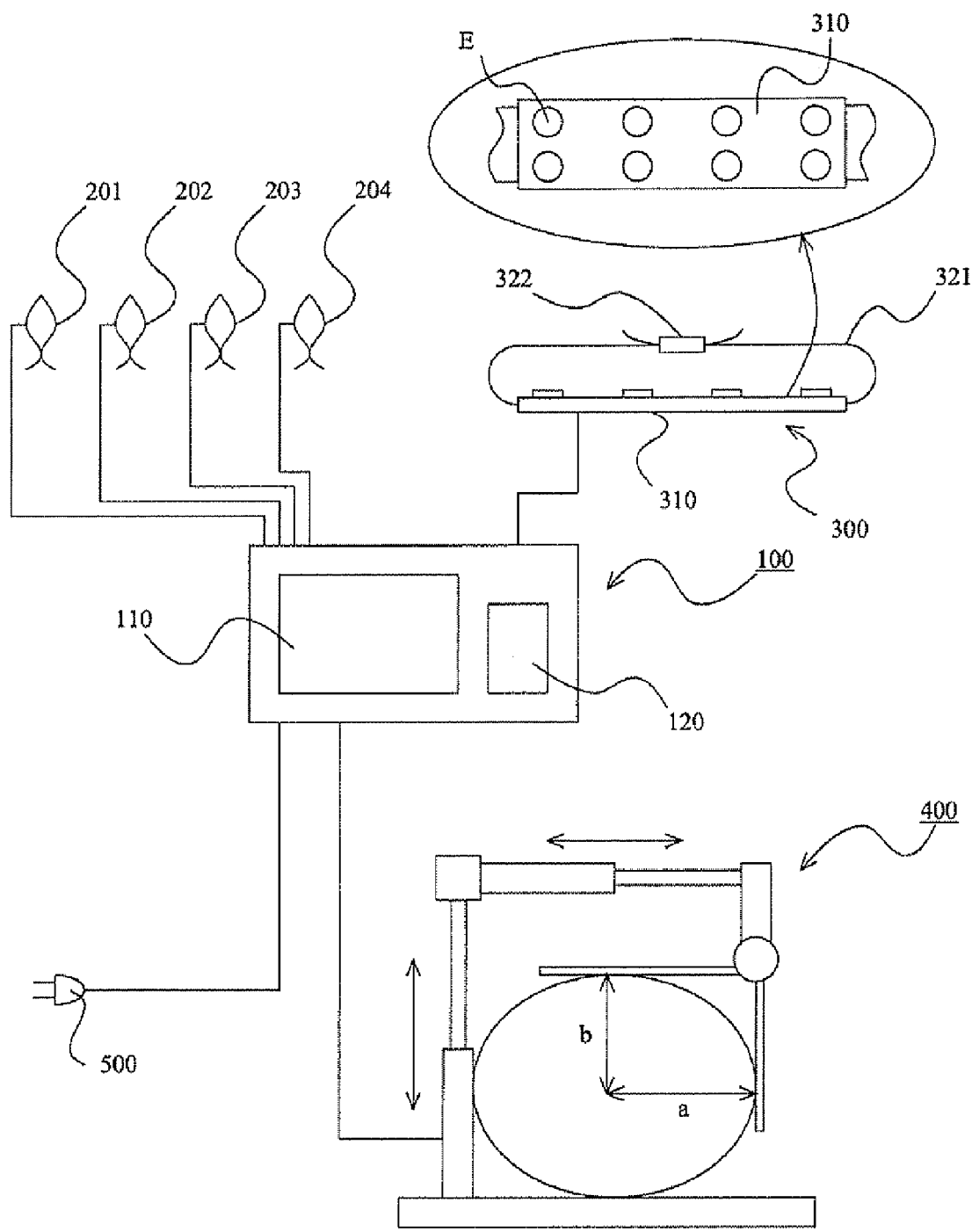
FIG. 3 is an entire configuration diagram of a visceral fat measuring device according to an embodiment of the present invention.

The entire configuration of the visceral fat measuring device according to the present embodiment will be described with reference to FIG. 3. FIG. 3 is an entire configuration diagram of the visceral fat measuring device according to the embodiment of the present invention.

The visceral fat measuring device according to the present embodiment is provided with a device main body 100, four clips 201, 202, 203, 204 for attaching electrodes to the hands and the legs, a belt 300 for attaching electrodes to the dorsal, a measuring unit 400 for measuring the vertical width and the horizontal width of the trunk, and a socket 500 for supplying electric power to the device main body 100.

The device main body 100 is provided with a display unit 110 for displaying various input information and the measurement result, and an operation unit 120 for turning on or off a power supply of the device main body 100 and inputting the various information.

The clips 201, 202, 203, 204 are respectively provided with the electrodes. By attaching these clips 201, 202, 203, 204 to the hands and the legs (preferably, wrists and ankles) so as to nip the hands and the legs, the electrodes can be closely attached to the hands and the legs. It should be noted that the electrodes respectively provided in the clips 201, 202, 203, 204 correspond to the electrodes EILa10, EIRa10, EILb10, EIRb10 shown in FIG. 1.

The belt 300 is provided with a pressed member 310 to be pressed onto the dorsal of the user subjected to the measurement, a belt portion 320 fixed to the both sides of the pressed member 310, and a buckle 330 for fixing the belt portion 320. The total of eight electrodes E are provided in the pressed member 310. By winding the belt 300 formed in such a way around a waist so that the pressed member 310 is abutted with a slightly upper part of coccyx, the eight electrodes E can be closely attached at positions on the back side of the abdominal part on the dorsal of the user. It should be noted that these eight electrodes E correspond to the eight electrodes EVa11, EVB11, EVa12, EVb12, EVa13, EVb13, EVa14, EVb14 shown in FIG. 1, and the eight electrodes EIa21, EIb21, EVa21, EVb21, EIa22, EIb22, EVa22, Evb22 shown in FIG. 2. That is, by switching the electric circuit in the device main body 100 between a case where the impedance Zt of the entire trunk is calculated and a case where the impedance Zs of the surface layer of the trunk is calculated, roles of the eight electrodes E can be changed.

The trunk width measuring unit 400 is provided with a plurality of contact portions. By bringing the contact portions into contact with the trunk, the horizontal width 2a and the vertical width 2b of the trunk can be measured in a state that the user lies on a bed. A detailed configuration will be described later. It should be noted that in the present embodiment, the horizontal width 2a and the vertical width 2b of the trunk can be obtained as electric information (data) based on positional information of the contact portions in the device main body 100. The trunk sectional area is calculated from the information relating to the horizontal width 2a and the vertical width 2b of the trunk obtained in such a way as described in the measurement principle of the visceral fat.

It should be noted that in the present embodiment, the visceral fat measuring device is provided with the trunk width measuring unit 400, and the vertical width and the horizontal width of the trunk and the trunk sectional area are automatically measured by this trunk width measuring unit 400. However, values obtained by other measurement devices or manual measurement and calculation can also be inputted into the device main body 100.

(Control Configuration of Visceral Fat Measuring Device)

Figure 4:
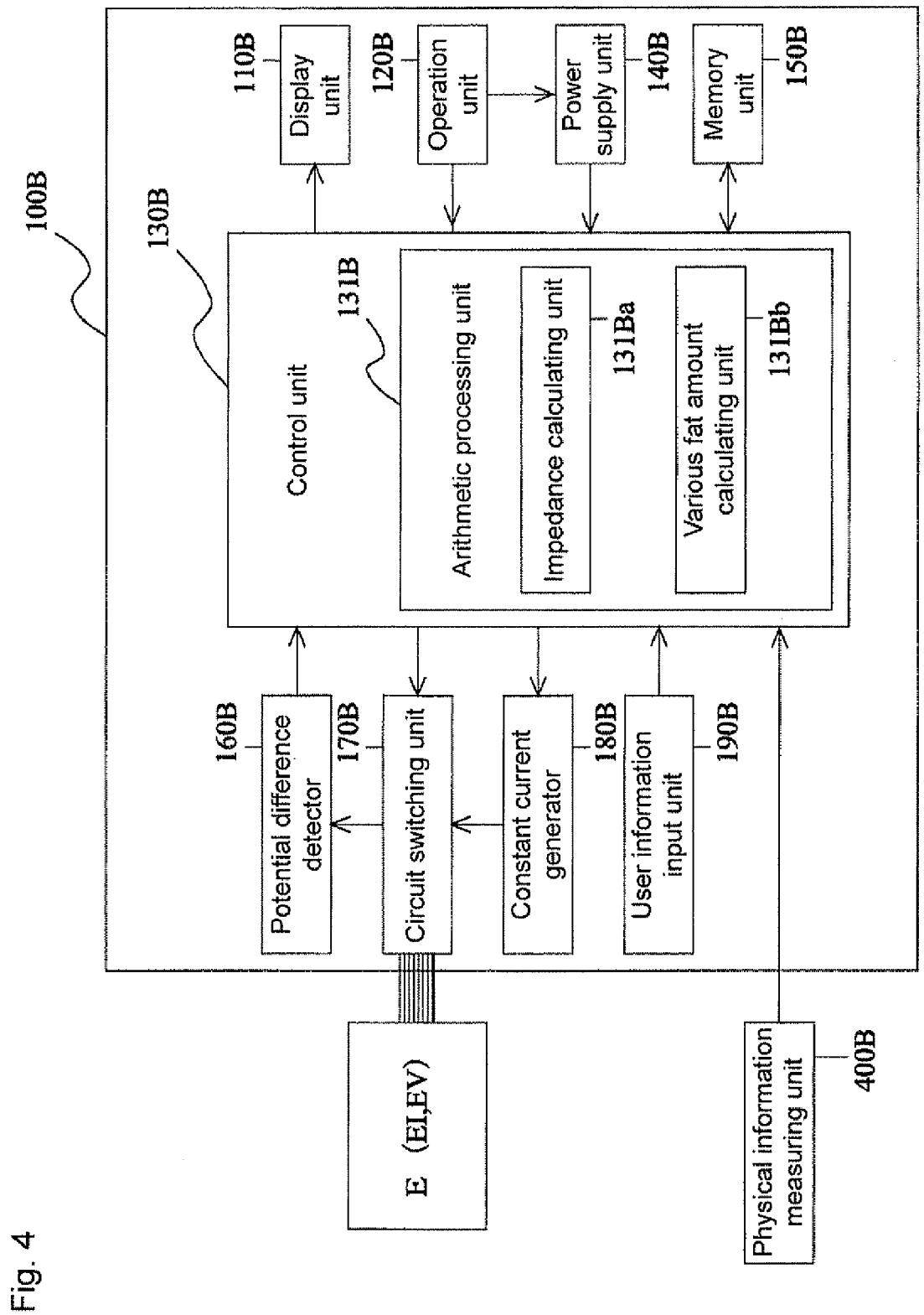
FIG. 4 is a control block diagram of the visceral fat measuring device according to the embodiment of the present invention.

A control configuration of the visceral fat measuring device according to the present embodiment will be described with reference to FIG. 4. FIG. 4 is a control block diagram of the visceral fat measuring device according to the embodiment of the present invention.

In the visceral fat measuring device according to the present embodiment, a device main body 100B is provided with a control unit (CPU) 130B, a display unit 110B, an operation unit 120B, a power supply unit 140B, a memory unit 150B, a potential difference detector 160B, a circuit switching unit 170B, a constant current generator 180B, and a user information input unit 190B.

The display unit 110B having a role of displaying input information from the operation unit 120B and the user information input unit 190B, the measurement result, and the like is formed by a liquid crystal display and the like. The operation unit 120B having a role of enabling the user or the like to input various information is formed by various buttons, a touchscreen, and the like. It should be noted that in the present embodiment, in addition to the input of the user information from the operation unit 120B, the user information is inputted from a barcode reader, a card reader, a USB memory, or the like via the user information input unit 190B.

The power supply unit 140B has a role of supplying the electric power to the control unit 10 and the like. When the power supply is turned on by the operation unit 120B, the electric power is supplied to the units, and when the power supply is turned off, the supply of the electric power is stopped. The memory unit 150B stores various data, programs, and the like for measuring the visceral fat.

The electrodes E respectively provided in the clips 201, 202, 203, 204 and the electrodes E provided in the belt are electrically connected to the circuit switching unit 170B provided in the device main body 100B. A physical information measuring unit 400B provided in the measuring unit 400 is electrically connected to the control unit 130B provided in the device main body 100B.

The control unit 130B has a role of controlling the entire visceral fat measuring device. The control unit 130B is provided with an arithmetic processing unit 131B. This arithmetic processing unit 131B is provided with an impedance calculating unit 131Ba for calculating impedance based on various information sent to the control unit 130B, and a various fat amount calculating unit 131Bb for calculating various fat amounts based on the calculated impedance.

The circuit switching unit 170B is for example formed by a plurality of relay circuits. This circuit switching unit 170B has a role of changing the electric circuit based on a command from the control unit 130B. That is, as described above, the circuit switching unit changes the electric circuit so as to have a circuit configuration shown in FIG. 1 in a case where the impedance information of the entire trunk is obtained, and to have a circuit configuration shown in FIG. 2 in a case where the impedance information of the surface layer of the trunk on the dorsal side is obtained.

The constant current generator 180B applies a high frequency current (of 50 kHz, 500 µA, for example) based on a command from the control unit 130B. More specifically, in a case of the electric circuit shown in FIG. 1, the electric current 110 is applied between the electrodes EILa10, EIRa10 and the electrodes EILb10, EIRb10. In a case of the electric circuit shown in FIG. 2, the electric currents I21, I22 are respectively applied between the electrode EIa21 and the electrode EIb21 and between the electrode EIa22 and the electrode EIb22.

The potential difference detector 160B detects a potential difference between predetermined electrodes while the electric current is applied by the constant current generator 180B. More specifically, in a case of the electric circuit shown in FIG. 1, the potential difference V11 is detected between the electrode EVa11 and the electrode EVb11, the potential difference V12 is detected between the electrode EVa12 and the electrode EVb12, the potential difference V13 is detected between the electrode EVa13 and the electrode EVb13, and the potential difference V14 is detected between the electrode EVa14 and the electrode EVb14. In a case of the electric circuit shown in FIG. 2, the potential difference V21 is detected between the electrode EVa21 and the electrode. EVb21, and the potential difference V22 is detected between the electrode EVa22 and the electrode EVb22.

The potential difference information detected by the potential difference detector 160B is sent to the control unit 130B. The physical information obtained by measurement by the measuring unit 400 is sent from the physical information measuring unit 400B to the control unit 130B of the device main body 100B. It should be noted that the physical information in the present embodiment is information relating to size of the horizontal width 2a and size of the vertical width 2b of the trunk.

In the arithmetic processing unit 131B in the control unit 130B, the impedance calculating unit 131Ba calculates the impedance Zt of the entire trunk and the impedance Zs of the surface layer of the trunk based on the potential difference information sent from the potential difference detector 160B. In the arithmetic processing unit 131B, the various fat amount calculating unit 131Bb calculates the various fat amounts (including the visceral fat sectional area) based on the calculated impedance Zt of the entire trunk and the impedance Zs of the surface layer of the trunk, the physical information sent from the physical information measuring unit 400B, and various information sent from the operation unit 120B and the user information input unit 190B.

Next, a measuring order in the visceral fat measuring device according to the present embodiment will be briefly described.

Firstly, the user subjected to the measurement of the visceral fat or a person who performs the measurement of the user turns on the power supply of the device main body 100 (100B) and inputs the user information. The vertical width and the horizontal width of the trunk of the user are measured by the measuring unit 400. Thereby, the information relating to the horizontal width 2a and the vertical width 2b of the trunk of the user is sent to the device main body 100 (100B). It should be noted that in the device main body 100 (100B), the trunk sectional area St ($=\alpha \times \pi \times a \times b$) is calculated based on the information. It should be noted that the value a is read from the memory unit 150B.

Next, the clips 201, 202, 203, 204 are attached to the hands and the legs of the user and the belt 300 is wound around the waist of the user. The measurement of the impedance is started.

In the present embodiment, firstly, the circuit switching unit 170B controls so as to have the electric circuit shown in FIG. 1. Thereby, the impedance Zt of the entire trunk is calculated by the impedance calculating unit 131Ba of the control unit 130B. The various fat amount calculating unit 131Bb calculates the lean body sectional area Sa ($=\beta \times a \times (1/Zt)$) from this calculated impedance Zt, the value a obtained by the measurement by the measuring unit 400, and the value $\beta$ stored in the memory unit 150B.

Next, the circuit switching unit 170B controls so as to have the electric circuit shown in FIG. 2. Thereby, the impedance Zs of the surface layer of the trunk is calculated by the impedance calculating unit 131Ba of the control unit 130B. The various fat amount calculating unit 131Bb calculates the subcutaneous fat sectional area Sb ($=\gamma \times a \times Zs$) from this calculated impedance Zs, the value a obtained by the measurement by the measuring unit 400, and the value $\gamma$ stored in the memory unit 150B.

The control unit 130B calculates the visceral fat sectional area Sx ($=$St$-$Sa$-$Sb) from the trunk sectional area St, the lean body sectional area Sa, and the subcutaneous fat sectional area Sb obtained as described above by the arithmetic processing unit 131B, and displays the values of the visceral fat sectional area Sx and the like on the display unit 110 (110B) as the measurement result. It should be noted that although a case where the various fat amount calculating unit determines the visceral fat sectional area Sx with using Sx=St$-$Sa$-$Sb is described in this measuring order, the visceral fat sectional area Sx may be determined with using Sx=St$-$Sa$-$Sb+$\delta$, Sx=St$-$F (Zt, Zs, a, b), or the like as described in the measurement principle of the visceral fat.

(Trunk Width Measuring Unit)

The trunk width measuring unit will be described further in detail with reference to FIGS. 5 to 8.

Figure 5:
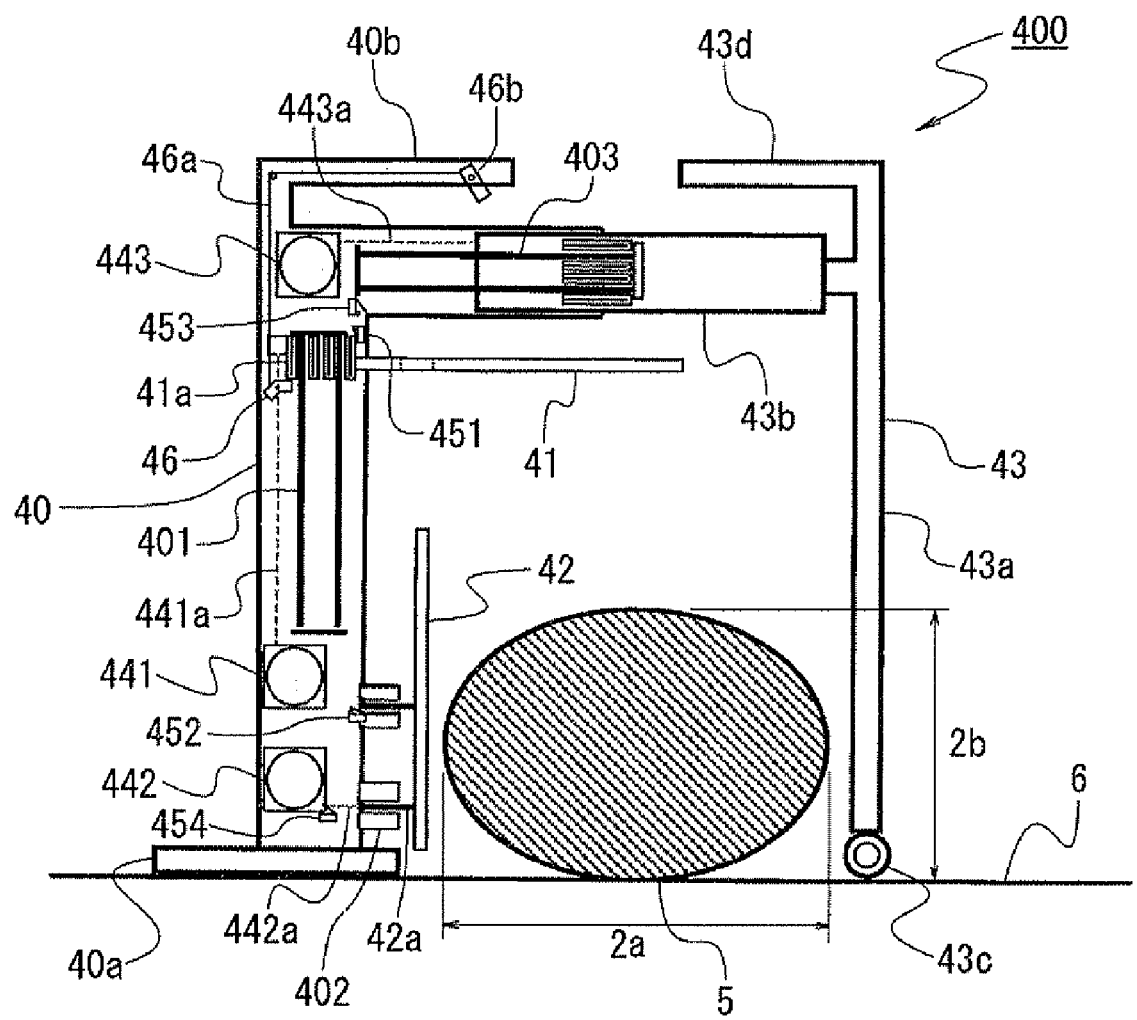
FIG. 5 is a schematic sectional view of a trunk width measuring unit according to the embodiment of the present invention.
Figure 6:
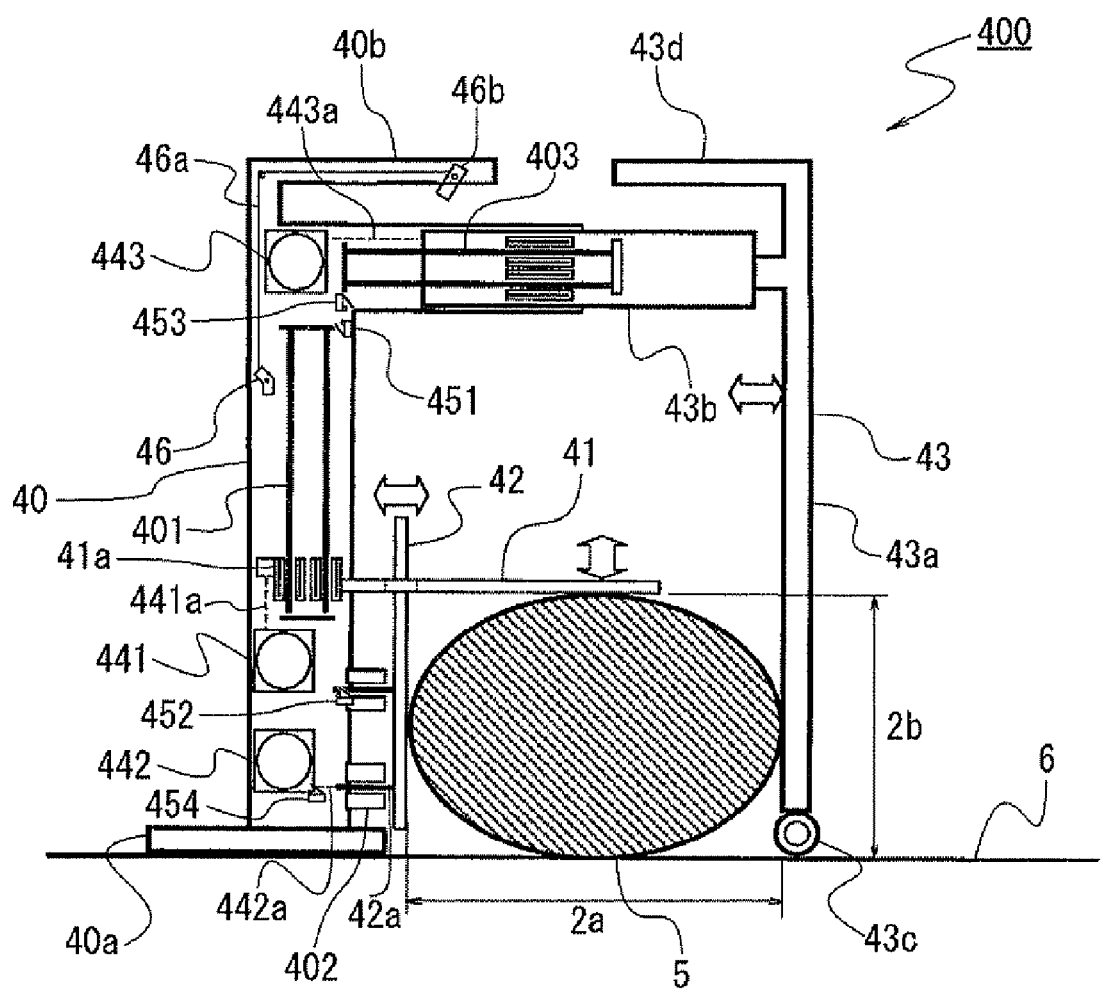
FIG. 6 is a schematic sectional view of the trunk width measuring unit according to the embodiment of the present invention.

In the present embodiment, the trunk width measuring unit 400 capable of measuring the vertical width and the horizontal width of the trunk of the user is provided as the physical information measuring unit 400B. FIG. 5 is a schematic sectional view of the trunk width measuring unit 400 showing a state before the contact portions are brought into contact with the trunk of the user. FIG. 6 is a schematic sectional view of the trunk width measuring unit 400 showing a state that the contact portions are in contact with the trunk of the user.

The trunk width measuring unit 400 is provided with a unit main body 40 positioned and mounted at a predetermined position on a bed 6 on which a user 5 lies in a supine position, and first, second and third contact portions 41, 42, 43 provided respectively movably relative to the unit main body 40.

The unit main body 40 is provided with rotary encoders 441, 442, 443 for detecting moving distances of the contact portions, microswitches 451, 452, 453 for detecting whether or not the contact portions are placed at original positions, an electronic circuit (not shown) in which a calculating unit for calculating the vertical width and the horizontal width of the trunk and the like are formed, a switch (not shown) for starting the measurement of the vertical width and the horizontal width of the trunk, and the like.

The first contact portion 41 is assembled so as to be raised and lowered in the vertical direction relative to the unit main body 40, and brought into contact with an upper surface (a front surface of the abdominal part) of the trunk of the user 5 in the supine position so as to measure the vertical width (thickness) of the trunk of the user 5. The first contact portion 41 is made of a plate shape material which is partly or entirely transparent or semi-transparent extending in the substantially horizontal direction, and designed to have light weight so that the trunk is not deformed when the first contact portion 41 is brought into contact with the trunk of the user 5.

A slide portion 41a is provided in a root of the first contact portion 41. The slide portion 41a is assembled slidably in the vertical direction relative to a rail portion 401 provided in the unit main body 40 so as to extend in the vertical direction.

Thereby, the first contact portion 41 can be raised and lowered in the vertical direction relative to the unit main body 40. The first contact portion 41 takes a highest position of the rail portion 401 as the original position. In a state that there is no support, the first contact portion is lowered to a lowermost point of the rail portion 401 by self-weight. Therefore, after brought into contact with the upper surface of the trunk, the first contact portion 41 is movable in the vertical direction while being supported on the upper surface of the trunk. Thereby, the first contact portion 41 can follow a change in a shape (the vertical width) of the trunk due to a change in a breathing state of the user.

The unit main body 40 is provided with a locking portion 46 for locking the first contact portion 41 at the highest position of the rail portion 401. The locking portion 46 is pulled and rotated by a wire 46a by switching an inclination of a lever 46b coupled via the wire 46a so as to release a locking state of the first contact portion 41. It should be noted that a configuration of a locking means is not limited to this but other locking mechanisms may be used.

A wire 441a extending from the rotary encoder 441 serving as a first detector is attached to the slide portion 41a of the first contact portion 41. By detecting a length of the wire 441a pulled by lowering the first contact portion 41 with the rotary encoder 441, a lowering distance of the first contact portion 41 can be detected. Since the conventional technology may be appropriately utilized for the rotary encoder, detailed description of a configuration thereof and the like is omitted. A means for detecting the moving distance is not limited to the rotary encoder but other devices capable of detecting the moving distance may be used.

The microswitch 451 serving as an original position sensor is arranged so that a movable contact point is pushed by the slide portion 41a and brought into contact with a fixed contact point when the first contact portion 41 is placed at the original position, that is, the highest position of the rail portion 401. Therefore, by connecting the movable contact point of the microswitch 451 and the fixed contact point so as to obtain the ON state, the fact that the first contact portion 41 is at the original position can be detected. Since the conventional technology may be appropriately utilized for the microswitch, detailed description of a configuration thereof and the like is omitted. A means for detecting the position of the contact portion is not limited to the microswitch described above but other devices capable of detecting the position may be used irrespective of a contact type or a non-contact type.

The second contact portion 42 and the third contact portion 43 are arranged so as to face each other in the horizontal direction, and brought into contact with side surfaces (sides) of the trunk so as to nip the trunk of the user 5 in the supine position and measure the horizontal width of the trunk of the user 5. The second contact portion 42 and the third contact portion 43 are assembled respectively movably in the horizontal direction relative to the unit main body 40 so that a facing distance between each other can be changed.

The second contact portion 42 is made of a plate shape material which is partly or entirely transparent or semi-transparent extending in the substantially vertical direction. The second contact portion 42 is provided with slide portions 42a protruding in the horizontal direction. The unit main body 40 is provided with guide portions 402 into which the slide portions 42a are insertable. The slide portions 42a are inserted into the guide portions 402 and slid in the horizontal direction relative to the guide portions 402, so that the second contact portion 42 is moved in the horizontal direction relative to the unit main body 40. In order not to deform the trunk when the second contact portion 42 is brought into contact with the trunk of the user 5, weight of the second contact portion 42, sliding resistance between the slide portions 42a and the guide portions 402, and the like are set so that reactive force that the trunk receives from the second contact portion 42 is sufficiently small.

The second contact portion 42 is biased in the facing direction to the third contact portion 43 (the trunk of the user 5) by a bias means such as a spring (not shown) so as to follow the change in the shape of the trunk due to a breathing action or the like. The bias means is formed to be sufficiently small so that bias force applied to the second contact portion 42 does not deform the trunk of the user. The second contact portion 42 is returned to the original position by the bias means when in contact with no members.

A wire 442a extending from the rotary encoder 442 serving as a second detector is attached to the slide portion 42b of the second contact portion 42. Therefore, the rotary encoder 442 detects pull-out length of the wire 442a changed by the movement of the second contact portion 42 so as to detect the moving distance of the second contact portion 42.

The microswitch 452 serving as an original position sensor is arranged so that a movable contact point is pushed by the slide portion 42a and brought into contact with a fixed contact point when the second contact portion 42 is placed at the original position. The original position of the second contact portion 42 is a position where the second contact portion 42 is most extended, that is, a one limit position of a movable region of the second contact portion 42 which is a position of a narrowest gap with the third contact portion 43. Although not shown in detail, the microswitch 452 is formed so that a contact state between the movable contact point and the fixed contact point is opened when the second contact portion 42 is pushed beyond the original position. Therefore, the microswitch 452 is in the ON state only when the second contact portion 42 is placed at the original position.

A position where the second contact portion 42 is brought into contact with the trunk of the user 5 at the time of measuring the horizontal width of the trunk is determined by an installation position of the unit main body 40 on the bed 6. Therefore, the position of the unit main body 40 is determined so that a contact position of the second contact portion 42 with the trunk serves as a position where the second contact portion is pushed beyond the original position to some extent. If the contact position of the second contact portion 42 with the trunk at the time of measuring is the original position where the second contact portion 42 is firstly brought into contact with the side surface of the trunk of the user 5, a contact state between the second contact portion 42 and the trunk of the user 5 is sometimes not maintained according to the breathing state at that time, and according to a change in breathing after that. That is, when the position of the contact at the time of exhalation when the horizontal width of the trunk is extended serves as a measurement position, the second contact portion 42 cannot follow the change in the shape of the trunk upon contraction of the horizontal width of the trunk at the time of inhalation, so that the second contact portion and the trunk are in a non-contact state. Accordingly, the horizontal width of the trunk at the time of inhalation cannot be measured, so that the breathing state cannot be reflected in the measurement of the horizontal width of the trunk. Therefore, the installation position of the unit main body 40 is determined so that the position where the second contact portion 42 is pushed to some extent and the contact state with the side surface of the trunk is maintained irrespective of the breathing state serves as the measurement position.

When the trunk of the user 5 is pressed beyond the movable region of the second contact portion 42, the trunk is deformed.

Therefore, as an excessive press sensor for detecting such excessive press, a microswitch 454 is provided in the unit main body 40 so that a movable contact point is pushed into the ON state by the second contact portion 42 when the second contact portion 42 is placed at a movable limit position. It should be noted that although detailed description such as the figure is omitted, notification means such as a buzzer for notifying the user 5 or an operator of the second contact portion 42 being excessively pressed onto the trunk when the microswitch 454 is in the ON state may be provided.

In the present embodiment, two pairs of the slide portions 42a and the guide portions 402 are provided. However, three pairs or more may be provided. In the present embodiment, one pair among the two pairs of the slide portions 42a and the guide portions 402 is provided with the microswitch 452 for detecting the original position, and the other pair is provided with the microswitch 454 for detecting the excessive press. However, the present invention is not limited to this. For example, the microswitch for the original position and the microswitch for detecting the excessive press may be provided in both the pairs.

The third contact portion 43 is formed by a plate shape portion 43a made of a material which is partly or entirely transparent or semi-transparent extending in the substantially vertical direction, and a slide portion 43b extending in the horizontal direction from an upper part of the plate shape portion 43a on the upper side of the trunk of the user 5. A caster 43c is provided in a lower end of the plate shape portion 43a. The slide portion 43b is assembled slidably in the horizontal direction relative to a rail portion 403 provided in the unit main body 40 so as to extend in the substantially horizontal direction. Although not shown in the figures or the like, the same means as the above bias means provided for the second contact portion 42 may be also provided for the third contact portion 43.

A wire 443a extending from the rotary encoder 443 serving as a third detector is attached to the slide portion 43b of the third contact portion 43. Therefore, the rotary encoder 443 detects pull-out length of the wire 443a changed by the movement of the third contact portion 43 so as to detect the moving distance of the third contact portion 43.

The microswitch 453 serving as an original position sensor is arranged so that a movable contact point is pushed by the slide portion 43b and brought into contact with a fixed contact point when the third contact portion 43 is placed at the original position. The original position of the third contact portion 43 is a position where the third contact portion 43 is most contracted relative to the unit main body 40, that is, a one limit position of a movable region of the third contact portion 43 which is a position of a narrowest gap with the second contact portion 42.

Gripping portions 40b, 43d for easily holding the trunk width measuring unit 4 so as to improve workability such as installation onto the bed 6 and positioning of the third contact portion 43 are respectively provided in upper parts of the unit main body 40 and the third contact portion 43. A lever 46b is provided in the gripping portion 40b of the unit main body 40. It should be noted that shapes of the gripping portions 40b, 43d, arrangement of the lever 46b, and the like are not limited to this. In order to prevent fall-down of the unit main body 40, a plate portion 40a for enlarging a ground area on the bed 6 is provided in a lower end of the unit main body 40.

It should be noted that although not shown in the figure, a pressure sensor capable of detecting reactive force that the contact portions receive from the trunk may be provided. Thereby, the contact state between the trunk and the contact portions such as whether or not the contact portions are excessively pressed onto the trunk can be determined based on magnitude of the reactive force that the contact portions receive from the trunk, and the breathing state of the user can be determined from a change in the reactive force.

Figure 7:
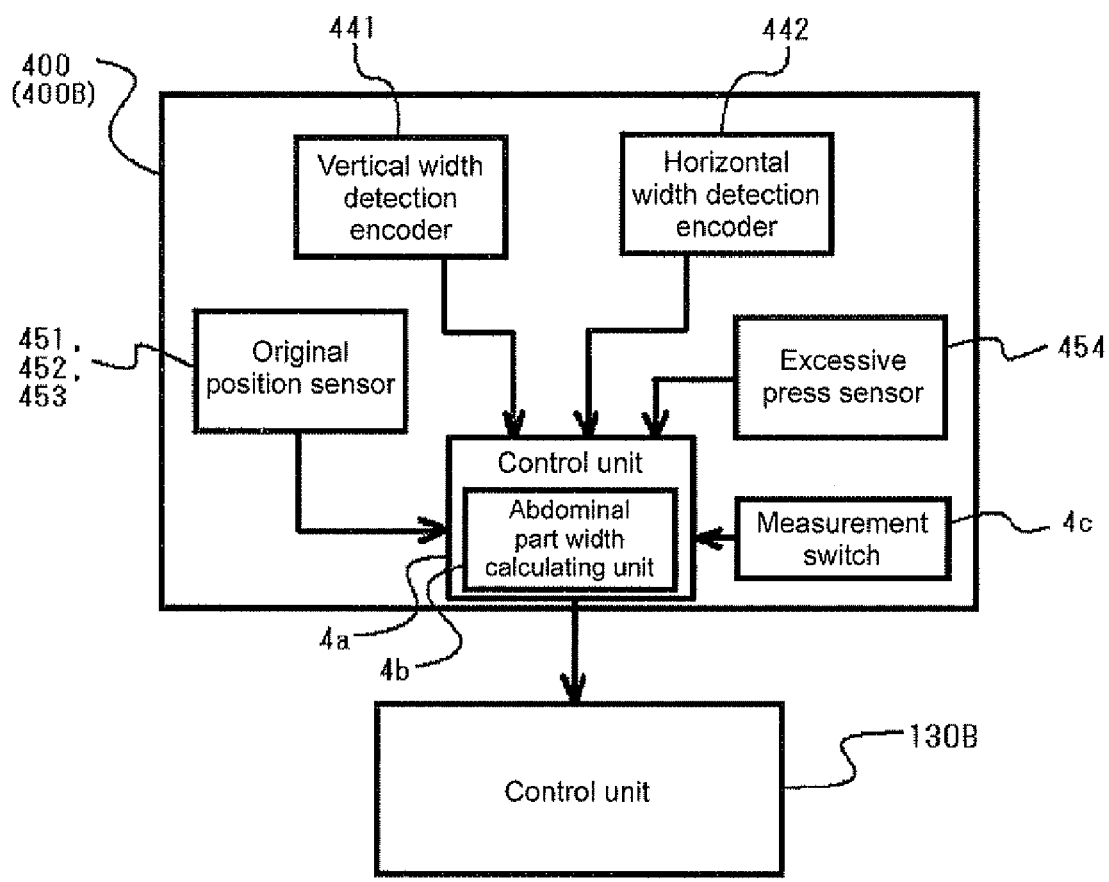
FIG. 7 is a functional block diagram of the trunk width measuring unit according to the embodiment of the present invention.

Next, a functional configuration of the trunk width measuring unit 400 (the physical information measuring unit 400B) will be described with reference to FIG. 7. FIG. 7 is a functional block diagram of the trunk width measuring unit of the visceral fat measuring device according to the embodiment of the present invention.

As shown in FIG. 7, the trunk width measuring unit 400 (the physical information measuring unit 400B) is mainly provided with a control unit 4a including a trunk width calculating unit 4b, a measurement switch 4c, a vertical width detection encoder 441, horizontal width detection encoders 442, 443, original position sensors 451, 452, 453, and an excessive press sensor 454.

The vertical width detection encoder 441 detects and outputs the lowering distance of the first contact portion 41 from the original position to the control unit 4a. The horizontal width detection encoders 442, 443 detect and output the moving distance of the second contact portion 42 from the original position and the moving distance of the third contact portion 43 from the original position to the control unit 4a.

The original position sensors 451, 452, 453 output whether or not the first contact portion 41, the second contact portion 42, and the third contact portion 43 are respectively placed at the original positions, that is, whether the microswitches forming the original position sensors 451, 452, 453 are in the ON state or the OFF state to the control unit 4a. The excessive press sensor 454 outputs whether or not the second contact portion 42 is placed at the movable limit position, that is, whether the microswitch forming the excessive press sensor 454 is in the ON state or the OFF state to the control unit 4a.

The control unit 4a is formed by for example a CPU (Central Processor Unit), and provided with the trunk width calculating unit 4b. The trunk width calculating unit 4b calculates the vertical width and the horizontal width of the trunk of the user based on the measurement values of the moving distances of the contact portions inputted from the vertical width detection encoder 441 and the horizontal width detection encoders 442, 443, and ON/OFF signals inputted from the original position sensors 451, 452, 453 and the excessive press sensor 454.

Calculation of the vertical width and the horizontal width of the trunk by the trunk width calculating unit 4b of the control unit 4a is performed after receiving a command of starting the calculation issued from the measurement switch 4c.

The control unit 4a outputs the vertical width and the horizontal width of the trunk calculated by the trunk width calculating unit 4b as the physical information to the control unit 130B of the visceral fat measuring device.

(Action of Trunk Width Measuring Unit)

Next, actions at the time of measuring the vertical width and the horizontal width of the trunk of the user by the trunk width measuring unit will be described with reference to FIG. 8.

Figure 8:
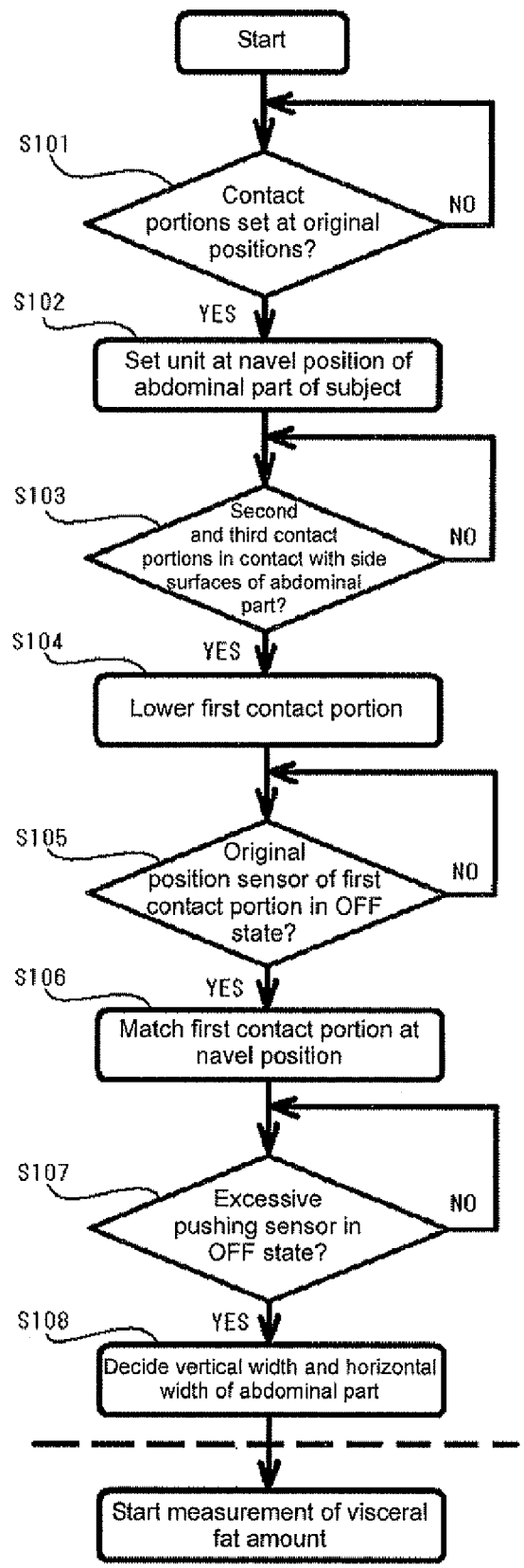
FIG. 8 is a flowchart showing a flow of operation and action processing of the trunk width measuring unit according to the embodiment of the present invention.

FIG. 8 is a flowchart showing a flow of operation and action processing of the trunk width measuring unit of the visceral fat measuring device according to the embodiment of the present invention. The processing shown in the flowchart of FIG. 8 is preliminarily stored in the memory unit 150B of the visceral fat measuring device or a memory unit (not shown) of the trunk width measuring unit 4 as a program. By reading out and executing the program by the control unit 4a, functions of the measurement processing of the vertical width and the horizontal width of the trunk are realized.

As shown in FIG. 8, the control unit 4a determines whether or not all the first contact portion 41, the second contact portion 42, and the third contact portion 43 are set at the original positions, that is, whether or not all the microswitches 451, 452, 453 serving as the original position sensors are in the ON state (Step S101). The control unit 4a stands by until all the contact portions are set at the original positions (NO in Step S101).

When all the contact portions are set at the original positions (YES in Step S101), the trunk width measuring unit 400 is installed on the bed 6 on which the user 5 in the supine position lies. Specifically, in order to arrange the second contact portion 42 and the third contact portion 43 on the both sides of the abdominal part, the third contact portion 43 is extended in the horizontal direction from the unit main body 40, so that the trunk width measuring unit 4 is installed to stride over a navel position of the trunk of the user 5 (Step S102). At this time, the control unit 4a starts the measurement of the horizontal width of the trunk from the moving distances of the second contact portion 42 and the third contact portion 43 detected by the rotary encoders 442, 443 for detecting the horizontal width.

Next, the control unit 4a determines whether or not the second contact portion 42 and the third contact portion 43 are respectively in contact with the side surfaces of the trunk (Step S103). In the present embodiment, whether or not the second contact portion 42 and the third contact portion 43 are both moved from the original positions and the microswitch 452 and the microswitch 453 serving as the original position sensors thereof are both in the OFF state is a factor for determining whether or not the second contact portion 42 and the third contact portion 43 are respectively in contact with the side surfaces of the trunk. The control unit 4a stands by until the microswitch 452 and the microswitch 453 are both in the OFF state (NO in Step S103).

When it is determined that the second contact portion 42 and the third contact portion 43 are respectively in contact with the side surfaces of the trunk (YES in Step S103), the lever 46b is pulled so as to release the locking state of the first contact portion 41 by the locking portion 46 and lower the first contact portion 41 from the original position (Step S104). At this time, the control unit 4a starts the measurement of the vertical width of the trunk from the lowering distance of the first contact portion 41 detected by the rotary encoder 441 for detecting the vertical width.

When the microswitch 451 serving as the original position sensor of the first contact portion 41 is in the OFF state and the lowering of the first contact portion 41 is confirmed (YES in Step S105), next, a contact position of the first contact portion 41 is confirmed. That is, whether or not the first contact portion 41 is in contact with the navel position of the trunk is confirmed from a transparent or semi-transparent part of the first contact portion 41. In a case where the contact position is displaced, an installation position of the unit 4 is corrected, so that the first contact portion 41 is matched with the navel position of the trunk.

Next, the control unit 4a determines whether or not the microswitch 454 serving as the excessive press sensor is in the OFF state, that is, whether or not the second contact portion 42 is excessively pressed onto the side surface of the trunk (Step S107). In a case where the microswitch 454 is in the ON state, the control unit 4a stands by until the microswitch is in the OFF state (NO in Step S107).

In a case where the microswitch 454 is in the OFF state (YES in Step S107) and the command of starting the measurement is issued by pushing the measurement switch 4c, the control unit 4a decides the vertical width and the horizontal width of the trunk of the user 5 based on the measurement values (Step S108).

In order to decide the vertical width and the horizontal width of the trunk, for example, maximum values, minimum values, and average values of the vertical width and the horizontal width of the trunk at the time of breathing are respectively calculated from the measurement values, and any of the values is made to be the vertical width and the horizontal width of the trunk.

As described above, the vertical width and the horizontal width of the trunk calculated and decided in such a way are outputted to the control unit 130B as the physical information at the time of measuring the visceral fat amount.

With the trunk width measuring unit according to the present embodiment, since the vertical width and the horizontal width of the trunk can be measured at the same breathing timing, the breathing state (at the time of inhalation or exhalation) can be reflected in measurement of the vertical width and the horizontal width of the trunk.

With the visceral fat measuring device according to the present embodiment, the visceral fat amount is calculated with using the two measurement values including the vertical width and the horizontal width of the trunk of the user as the physical information of the user. Therefore, an influence of the change in the shape of the trunk due to breathing is reduced, so that measurement precision can be improved.

Being different from the above conventional technology, the electrodes for measuring the impedance information are separated from the trunk width measuring unit for measuring the vertical width and the horizontal width of the trunk. Therefore, unlike the conventional technology, there is no need for pressing the contact portions to be brought into contact with the trunk onto the surface of the trunk so that the electrodes are closely attached to the surface of the trunk but the contact portions are only required to be in contact with the surface of the trunk. Thereby, deformation of the trunk due to contact of the contact portions for the measuring the vertical width and the horizontal width of the trunk can be suppressed, so that generation of varied calculated values of the shape of the trunk can be suppressed.

Since the vertical width and the horizontal width of the trunk can be measured at the same breathing timing, the breathing state (at the time of inhalation or exhalation) can be reflected in the measurement of the vertical width and the horizontal width of the trunk. Since the contact portions are formed so as to follow the change in the shape of the trunk at the time of breathing of the user, the breathing state can be more precisely reflected in the measurement of the vertical width and the horizontal width of the trunk, so that the measurement precision can be improved.

In the above embodiment, a case where the trunk width measuring unit is used for the visceral fat measuring device is described. However, a device for which the trunk width measuring unit according to the present embodiment is used is not limited to this. Needless to say, the trunk width measuring unit can be applied to various measuring devices using the vertical width and the horizontal width of the trunk as the physical information.

DESCRIPTION OF SYMBOLS 100, 100B: Device main body
110, 110B: Display unit
120, 120B: Operation unit
130B: Control unit 131B: Arithmetic processing unit
131Ba: Impedance calculating unit
131Bb: Various fat amount calculating unit
140B: Power supply unit
150B: Memory unit
160B: Potential difference detector
170B: Circuit switching unit
180B: Constant current generator
190B: User information input unit
201, 202, 203, 204: Clip
300: Belt
310: Pressed member
321: Belt portion
322: Buckle
400: Trunk width measuring unit
400B: Physical information measuring unit
40: Unit main body
41: First contact portion
42: Second contact portion
43: Third contact portion
441, 442, 443: Rotary encoder
451, 452, 453: Microswitch
500: Socket
E: Electrode

The invention claimed is:

1. A trunk width measuring unit, comprising:
a first contact portion to be brought into contact with an upper surface of a trunk of a user in a supine position;
a second contact portion to be brought into contact with one of side surfaces of the trunk;
a third contact portion to be brought into contact with the other side surface of the trunk;
a unit main body in which the first contact portion is attached movably in a vertical direction, the second contact portion and the third contact portion are attached movably in a horizontal direction, and the second contact portion or the third contact portion is placed at a position where the second contact portion or the third contact portion is brought into contact with the side surface of the trunk of the user; and
a trunk width calculating unit for calculating vertical width and horizontal width of the trunk, the trunk width calculating unit calculating the height from a plane on which the user lies to a contact position of the first contact portion based on a distance between the second contact portion and the third contact portion, wherein
the first contact portion is attached to the unit main body so as to be lowered by self-weight of the first contact portion and moved in the vertical direction relative to the unit main body in a state that the first contact portion is disposed on the upper surface of the trunk of the user, and the first contact portion is thus movable so as to follow a change in a shape of the trunk based on breathing of the user.

2. The trunk width measuring unit according to claim 1, further comprising:
a first detector for detecting a lowering distance of the first contact portion from a first original position on an upper side of the trunk of the user to a contact point with the upper surface of the trunk;
a second detector for detecting a moving distance of the second contact portion from a second original position in the horizontal direction; and
a third detector for detecting a moving distance of the third contact portion from a third original position in the horizontal direction, wherein
the trunk width calculating unit calculates the height from the plane on which the user lies to the contact position of the first contact portion based on the moving distance of the first contact portion detected by the first detector, and calculates a distance between the second contact portion and the third contact portion based on the moving distance of the second contact portion detected by the second detector and the moving distance of the third contact portion detected by the third detector.

3. The trunk width measuring unit according to claim 2, wherein
one of the second contact portion and the third contact portion is biased in the facing direction to the other of the second contact portion and the third contact portion and thus movable so as to follow the change in the shape of the trunk based on breathing of the user.

4. The trunk width measuring unit according to claim 2, including:
at least one original position sensor for detecting whether or not the first contact portion, the second contact portion and/or the third contact portion is placed at the at least one original position.

5. The trunk width measuring unit according to claim 1, including:
a sensor for detecting whether or not the second contact portion or the third contact portion is placed at a movable limit position.

6. The trunk width measuring unit according to claim 1, including:
a pressure sensor for detecting reactive force that the first contact portion, the second contact portion and/or the third contact portion receives from the trunk of the user.

7. The trunk width measuring unit according to claim 1, wherein
part or all of the first contact portion, the second contact portion and/or the third contact portion is formed by a transparent or semi-transparent member.

8. The trunk width measuring unit according to claim 1, wherein
the trunk width calculating unit calculates maximum values, minimum values, and average values of the vertical width and the horizontal width of the trunk based on breathing from the moving distances of the first contact portion, the second contact portion and the third contact portion, and any of the values are measurement values of the vertical width and the horizontal width of the trunk.

9. A visceral fat measuring device, comprising:
the trunk width measuring unit according to claim 1, wherein
a visceral fat amount is calculated based on:
a trunk sectional area in a section on an abdominal part of the trunk vertical to a body axis of the trunk, the trunk sectional area being calculated from the vertical width and the horizontal width of the trunk obtained using the trunk width measuring unit;
impedance information of an entire portion of the trunk obtained by applying an electric current from hands and legs to the trunk and measuring a potential difference in part of a surface of the trunk; and
impedance information of a surface layer of the trunk obtained by applying the electric current along the surface layer of the trunk and measuring a potential difference in part of the surface of the trunk.

* * * * *